United States Patent [19]

Heinemann et al.

[11] Patent Number: 4,695,566

[45] Date of Patent: Sep. 22, 1987

[54] 3-AMINOCARBONYLMETHOXY-5-PHENYLPYRAZOLE COMPOUNDS, ANTIARRYTHMIC COMPOSITIONS CONTAINING THEM, AND INTERMEDIATES IN THEIR PREPARATION

[75] Inventors: Henning Heinemann; Wolfgang Kehrbach; Uwe Schoen; Gerd Buschmann, all of Hanover; Ulrich Kuhl, Gehrden, all of Fed. Rep. of Germany

[73] Assignee: Kali-Chemie Pharma GmbH, Hanover, Fed. Rep. of Germany

[21] Appl. No.: 751,045

[22] Filed: Jul. 2, 1985

[30] Foreign Application Priority Data

Jul. 4, 1984 [DE] Fed. Rep. of Germany ....... 3424586

[51] Int. Cl.$^4$ ................ A61K 31/415; A61K 31/535; C07D 231/20; C07D 405/12
[52] U.S. Cl. .................................... 514/234; 514/326; 514/407; 544/140; 546/211; 548/369; 548/374; 548/375
[58] Field of Search ......................... 544/140; 546/211; 548/369, 374, 375; 514/234, 326, 407

[56] References Cited

U.S. PATENT DOCUMENTS 3,962,453 6/1976 Ahrens et al. .................... 548/375

FOREIGN PATENT DOCUMENTS 0007019 1/1980 European Pat. Off. ............ 548/375
2809183 9/1978 Fed. Rep. of Germany ...... 548/375
1567448 5/1980 United Kingdom ............... 548/375

*Primary Examiner*—Henry R. Jiles
*Assistant Examiner*—Kurt G. Briscoe
*Attorney, Agent, or Firm*—Schwartz, Jeffery, Schwaab, Mack, Blumenthal & Evans

[57] ABSTRACT

3-(aminoalkylaminocarbonylmethoxy)-5-phenylpyrazole compounds corresponding to the formula:

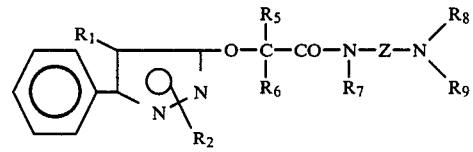

in which $R_1$, $R_2$, $R_5$, $R_6$, $R_7$, and $R_8$ and $R_9$ may be hydrogen or lower alkyl groups, or $R_5$ with $R_6$ and/or $R_8$ with $R_9$ may also form specified cyclic groups, $R_3$ and $R_4$ may be hydrogen, halogen, lower alkyl, lower alkoxy, trifluoromethyl, nitro, hydroxy or alkylene dioxy, and Z represents an alkylene chain or the 2-hydroxypropylene chain. The compounds possess pharmacological, in particular antiarrhythmic, properties.

16 Claims, No Drawings

3-AMINOCARBONYLMETHOXY-5-PHENYL-PYRAZOLE COMPOUNDS, ANTIARRYTHMIC COMPOSITIONS CONTAINING THEM, AND INTERMEDIATES IN THEIR PREPARATION

BACKGROUND OF THE INVENTION

This invention relates to new 3-(aminoalkylaminocarbonylmethoxy)-5-phenylpyrazole compounds and their salts and pharmaceutical compositions containing these compounds, as well as methods for the preparation of these compounds.

3-hydroxycarbonylmethoxy-5-phenylpyrazole compounds and their esters and amides with blood lipid lowering properties have been described in the specification of European Patent Application No. 7019.

SUMMARY OF THE INVENTION

It is an object of the present invention to develop new 3-carbonylmethoxy-5-phenylpyrazole compounds with valuable pharmacological properties.

It has now been found that the new 5-phenylpyrazole compounds, substituted in position 3 by an aminoalkylaminocarbonyl radical, possess valuable pharmacological properties and distinguish themselves in particular by marked antiarrhythmic effects and an advantageous activity profile. Owing to their pharmacological effects, the new compounds are suitable as medicaments, particularly for the treatment and prophylaxis of heart rhythm disorders.

According to the present invention there are provided new 3-aminocarbonylmethoxy-5-phenylpyrazole compounds of the general Formula I

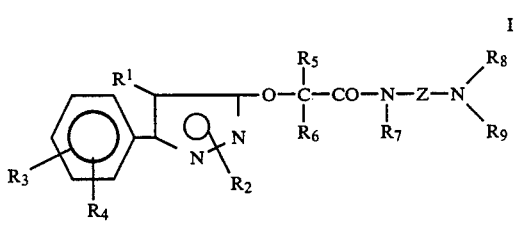

in which
$R_1$ is hydrogen or lower alkyl,
$R_2$ is in position 1 or 2 on the pyrazole ring and is hydrogen or lower alkyl,
$R_3$ is hydrogen, halogen, lower alkyl or lower alkoxy and
$R_4$ is hydrogen, halogen, lower alkyl, lower alkoxy or, if $R_3$ is hydrogen, $R_4$ may also be trifluoromethyl, nitro or hydroxy or
$R_3$ and $R_4$ are linked to adjacent carbon atoms and together represent an alkylene dioxy group with 1 or 2 carbon atoms,
$R_5$ is hydrogen or lower alkyl and
$R_6$ is hydrogen or methyl or
$R_5$ and $R_6$ together form an alkylene chain with 3 to 5 carbon atoms,
$R_7$ is hydrogen or lower alkyl,
Z is an alkylene chain with 2 to 5 carbon atoms or the 2-hydroxypropylene chain,
$R_8$ is hydrogen or lower alkyl and
$R_9$ is hydrogen or lower alkyl or
$R_8$ and $R_9$ together with the nitrogen atom to which they are linked represent a heterocyclic group of the general formula a

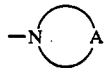

in which A is an alkylene chain with 4 or 5 carbon atoms which chain may be substituted by 1 or 2 methyl groups, or A is the $—C_2H_4—O—C_2H_4—$ chain, or if Z is an alkylene chain, then $R_8$ may be hydrogen or lower alkyl and
$R_9$ may be an alkylene chain, which together with the nitrogen atom to which it is linked and the carbon atom of the alkylene chain Z which is adjacent to this nitrogen atom, forms a 5- or 6-membered heterocycle;

and the acid addition salts of said components of the general formula I.

In the compounds of Formula I, where the substituent groups $R_1$ to $R_9$ represent or contain lower alkyl or alkoxy groups, these may be straight chain or branched groups with preferably 1 to 4 carbon atoms; the lower alkyl group is more preferably a methyl or ethyl group.

$R_1$ is preferably hydrogen, and if $R_1$ is a lower alkyl group, this is preferably a methyl or ethyl group. $R_2$ is preferably hydrogen, and if $R_2$ is lower alkyl group, this is preferably the methyl group.

Of the substituent groups $R_3$ and $R_4$ on the phenyl ring, the preferred lower alkyl and alkoxy groups are methyl and methoxy groups, while the preferred halogens are fluorine, chlorine, and bromine, most preferably fluorine. Preferably, $R_3$ and/or $R_4$ represent hydrogen or also fluorine, chlorine or methyl.

$R_5$ is advantageously a lower alkyl group with 1 to 4, preferably 1 or 2 carbon atoms, which is preferably a primary, straight-chained group. Preferably $R_5$ and $R_6$ are each methyl. If $R_5$ contains at least 2 carbon atoms, $R_6$ is preferably hydrogen. If $R_5$ and $R_6$ together form an alkylene chain, this is preferably a propylene chain. Advantageously $R_5$ and $R_6$ together contain 2 or 3 carbon atoms. $R_7$ is preferably hydrogen and if $R_7$ is an alkyl group, this is preferably hydrogen and if $R_7$ is an alkyl group, this is preferably a primary alkyl group with 1 to 4, most preferably 1 or 2 carbon atoms.

If Z represents an alkylene chain, this is preferably a straight chain with 2 or 4 carbon atoms.

If $R_8$ and/or $R_9$ are/is lower alkyl, these may be straight or branched and contain 1 to 4, preferably 1 or 2 carbon atoms. Advantageously, at least one of the substituent groups $R_8$ and $R_9$ is a lower alkyl group or is part of a heterocyclic ring. Desirably, the $—NR_8R_9$ group is a preferably unbranched dialkylamino group, particularly the diethylamino group. Examples of heterocyclic rings formed from the radical $R_9$ and the nitrogen atom, to which it is linked, together with the radical $R_8$ or the C-atom of the alkylene chain Z adjacent to the nitrogen, include piperidine, morpholine and pyrrolidine rings.

The new 3-aminocarbonylmethoxy-5-phenylpyrazole compounds of formula I and their acid addition salts are obtained according to the invention in that in a manner known per se (a) a compound of the general Formula II or III

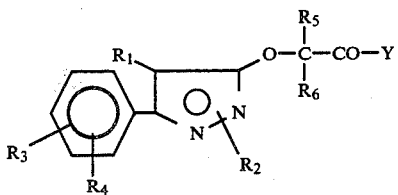

II

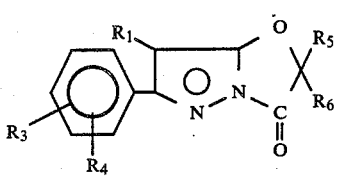

III in which $R_1$, $R_2$ $R_3$ and $R_4$ have the above defined meanings, and/or a 5-phenylpyrazolin-3-one compound tautomeric therewith is reacted with a compound of the general Formula VII

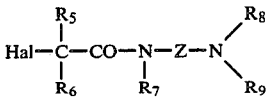

VII in which $R_5$, $R_6$, $R_7$, Z, $R_8$ and $R_9$ have the above defined meanings and Hal is halogen, or (d) for the preparation of a compound of the general Formula Ia

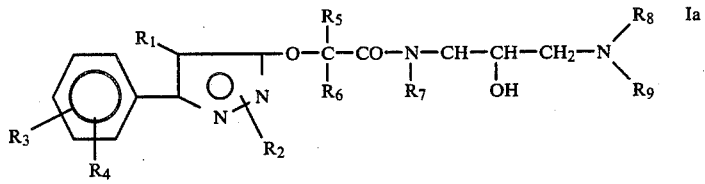

Ia in which $R_1$, $R_2$, $R_3$, $R_4$ $R_5$, $R_6$, $R_7$, $R_8$ and $R_9$ have the above defined meanings, a compound of the general in which $R_1$, $R_2$, $R_3$, $R_4$, $R_5$ and $R_6$ have the above defined meanings and Y is a reactive group, is reacted with a compound of the general Formula VIII

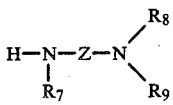

VIII in which $R_7$, Z, $R_8$ and $R_9$ have the above defined meanings, or (b) a compound of the general Formula IV

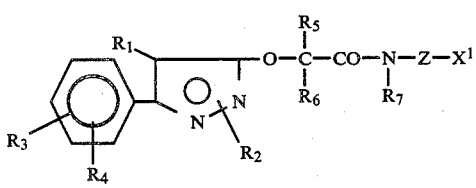

IV in which $R_1$, $R_2$, $R_3$, $R_4$, $R_5$, $R_6$, $R_7$ and Z have the above defined meanings and $X^1$ is a group which can be split off aminolytically, is reacted with an amino compound of the general Formula V

V in which $R_8$ and $R_9$ have the above defined meanings, or (c) a compound of the general Formula VI

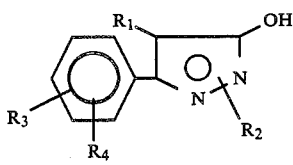

VI

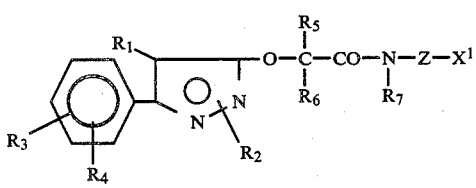

IX in which $R_1$, $R_2$, $R_3$, $R_4$, $R_5$, $R_6$ and $R_7$ have the above defined meanings, is reacted with a compound of the general Formula V

V

If $R_4$ in the resulting compound of the general Formula I is methoxy, the methoxy group is optionally split to form the hydroxy group. If the compound of formula I is obtained in the form of the free compound, it is optionally converted into an acid addition salt or if the compound of formula I is obtained in the form of an acid addition salt the salt is optionally converted into the free compound of Formula I.

DETAILED DESCRIPTION OF THE PREFERRED EMBODIMENTS

For carrying out the reaction according to process variant (a), the acids or acid derivatives of Formula II or, insofar as compounds are concerned in which $R_2$ is hydrogen, the cyclicized acid derivatives of Formula III or mixtures of compounds of Formulae II and III may be used.

The reaction of the acid or acid derivative of Formulae II or III with the diamine of Formula VIII may be carried out by methods conventional per se for the formation of amide groupings through aminoacylation. The compound of Formula II may be in the form of the acid (Y=OH) or a reactive derivative of the acid, in which Y is a reactive group, or a cyclic derivative of the acid of Formula III. Examples of reactive derivatives of formula II, include acid halides, preferably acid chlorides, esters, and mixed anhydrides, e.g., compounds of Formula II, in which the reactive group Y denotes halogen, preferably chlorine or bromine, lower alkoxy, preferably alkoxy with 1 to 4 carbon atoms, or a group O-W, in which W is a lower alkylcarbonyl or lower alkoxycarbonyl group or an organic sulphonic acid radical, particularly the radical of a lower alkane sulphonic acid, such as, for example, methane sulphonic acid or an aromatic sulphonic acid, such as benzene sulphonic acid or benzene sulphonic acids substituted by lower alkyl or halogen.

If an acid of Formula II itself is used, the reaction is advantageously carried out in the presence of a coupling reagent known to be suitable for amide formation. Suitable coupling reagents, which promote amide formation in that they react with the acid in situ with the formation of a reactive acid derivatives, are known from peptide chemistry. The following may be mentioned as examples of suitable coupling reagents: alkylcarbodiimides, preferably cycloakylcarbodiimides such as dicyclohexylcarbodiimide, carbonyldiimidazole and N-lower alkyl-2-halopyridinium salts, particularly halides or tosylates, preferably N-methyl-2-chloropyridiniumiodide (see, for example, Mukaiyama in 'Angew. Chemie' 91, pages 789 to 812). The reaction in the presence of a coupling reagent may suitably be carried out at temperatures from $-30°$ C. up to ambient temperature using solvents such as halogenated hydrocarbons and/or aromatic solvents optionally in the presence of an acid-binding amide.

The preferred compounds of Formula II include esters or acid halides, particularly acid chlorides, or mixed acid anhydrides, particularly those obtained by the reaction of an acid of Formula II with an organic sulphonic acid chloride, such as methane sulphonic acid chloride, or mixed anhydrides obtained by reaction with an ester of chloroformic acid. Alternatively cyclic derivatives of Formula III may be used. The reaction of the amide with the acid halide, acid anhydride and/or with a cyclic derivative of Formula III is carried out in the presence of an inert organic solvent, for example, a halogenated hydrocarbon such as methylene chloride, a cyclic or open ether such as dioxane or diethyl ether, dimethylformamide, sulpholane, tetramethyl carbamide or mixtures of these solvents and, optionally aromatic hydrocarbons such as benzene or toluene. Insofar as acid halides or acid anhydrides of Formula II are used, it is desirable to carry out the reaction in the presence of an acid-binding agent. The following are suitable examples of acid-binding agents: inorganic bases, for example alkali metal carbonates or hydroxides, or organic bases, particularly tertiary lower alkylamines, e.g., triethylamine or pyridine. In place of an added base, an excess of the amine of Formula VIII may also be used. Organic bases used in excess may also serve, at the same time, as solvents. In addition, it may be advantageous to add catalytic quantities of basic pyridines such as 4-dimethylaminopyridine or 4-pyrrolidinopyridine. Advantageously, the reaction is carried out at a temperature of from $-30°$ C. to the boiling temperature of the reaction mixture. The selected temperature may vary depending upon the initial compounds used; for example, in using acid halides or acid anhydrides of Formula II and cyclic derivatives of Formula III, low temperatures of up to approximately ambient temperatures are preferred.

It is particularly advantageous to react an intensively cooled solution of the acid derivatives of formula II or III with a solution of the amine of Formula VIII. If the amine contains a second reactive amine function, it is desirable to gradually add the solution of the acid derivative to the amine solution.

If the starting material is a compound of Formula II, in which $R_2$ is hydrogen, the compound may be partially converted, under the above-mentioned reaction conditions, into the corresponding cyclic compound of Formula III, which then further reacts with the amine of Formula VIII.

The reaction of compounds of Formula IV with amines of Formula V according to method variant (b) may be carried out according to methods which are conventional per se in aminoalkylation. Suitable examples of aminolytically replaceable radicals $X^1$ in the compounds of Formula IV include halogens such as chlorine, bromine and iodine, and organic sulphonic acid radicals, in particular radicals of lower alkyl sulphonic acids such as, for example, methane sulphonic acid or radicals of aromatic sulphonic acids, such as benzene sulphonic acid or benzene sulphonic acids substituted by lower alkyl or halogen, e.g., toluene sulphonic acids or bromobenzene sulphonic acids.

Advantageously, reaction (b) is carried out in an organic solvent which is inert under the reaction conditions. Suitable solvents include aromatic hydrocarbons such as benzene, toluene or xylene, cyclic ethers such as dioxane, dimethylformamide, sulpholane, tetramethylcarbamide or dimethylsulphoxide. Advantageously, an excess of the amine of Formula V is used as an acid-binding agent. An excess of the amine may also serve as solvent. If desired, inorganic bases may also be added as acid-binding agents. Suitable inorganic bases include, for example, alkali metal carbonates and bicarbonates.

The reaction according to method variant (c) represents an alkylation, known per se, at the oxygen atom in position 3 of the 3-hydroxypyrazole or of the pyrazolin-3-one tautomeric therewith. The reaction takes place advantageously under basic conditions in the inert solvent, for example, dimethylformamide, a cyclic ether such as dioxane, tetramethylcarbamide, dimethylsulphoxide, an aromatic hydrocarbon such as toluene or a mixture of two or more thereof. In organic bases such as alkali metal carbonates or hydroxides are particularly suitable as basis. Advantageously, approximately equivalent quantities of the compound of Formula VI and of the inorganic base are used. If desired, the compound of Formula VII may also be reacted with an alkali metal salt of the compound of Formula VI which may be produced in situ through reaction of the compound of Formula VI in one of the abovementioned solvents with an alkali metal hydride. The reaction preferably takes place at a temperature of from 0° C. up to the boiling temperature of the solvent, preferably at a temperature of from 0° to 100° C.

The reaction of a compound of Formula IX with a compound of Formula V according to method variant (d) may take place in a manner conventional in the reaction of epoxides. Advantageously, the reaction is carried out in an organic solvent which is inert under the reaction conditions, at a temperature from approximately 0° C. to approximately 100° C. The following are examples of suitable solvents: aromatic hydrocarbons such as benzene, toluene or xylene, open or cyclic ethers such as, for example, diethylether, tetrahydrofuran or dioxane, and lower alcohols.

In compounds of Formula I, in which $R_4$ is methoxy, the methoxy group may be split by methods suitable for the splitting of methoxyaryl ethers, in a manner known per se, to form a hydroxy group. For example, the ether decomposition may take place by treatment with hydrogen iodide in acetic anhydride or with lithium iodide in a pyridine, e.g., 2,4,6-trimethylpyridine.

If the initial compounds contain free hydroxy groups, these may, if desired, be provided with a protective group prior to the above reactions in a manner known per se, which group can easily be split off afterward. Suitable protective groups are known, for example, from E. McOmie "Protective Groups in Organic Chemistry" Plenum Press 1971. Hydrolytically or hydrogenolytically separable ethers such as tetrahydropyranyl ether or benzyl ether are suitable, for example, for the protection of a hydroxy group.

The compounds of formula I may be isolated from the reaction mixture, in a manner known per se, and purified. Acid addition salts may be converted into the free bases in a conventional manner and these may be converted, if desired, in a known manner into pharmacologically acceptable acid addition salts. The following are examples of suitable pharmacologically acceptable acid addition salts of compounds of Formula I: salts with inorganic acids such as hydrochloric acid, sulphuric acid and phosphoric acid, and salts with organic acids such as methane sulphonic acid, ethane sulphonic acid, cyclohexylaminosulphonic acid, aminosulphonic acid, acetic acid, maleic acid, fumaric acid, lactic acid, tartaric acid, phenylacetic acid and mandelic acid. The starting compounds of Formulae II and VI are known, or may be produced according to methods known as per se.

It is known that the compounds of Formula VI exist in several tautomeric forms, and that in addition to the enol form of the 5-phenylpyrazole-3-ols reproduced in Formula VI, the corresponding keto form of the 5-phenylpyrazoline-3-ones also exists. In general, mixtures of the various tautomeric forms are present, the composition of which may vary depending upon the nature of the substituent groups. Both forms, or their mixtures, may be used in preparing compounds of Formula I according to the invention. In the present specification, compounds of Formula VI therefore include all tautomeric forms of these compounds.

Compounds of Formula VI may be obtained by methods known per se for the production of 5-phenylpyrazoline-3-ones through cyclizing condensation of optionally substituted hydrazines of Formula XII $$NH_2-NHR_2 \qquad XII$$

in which $R_2$ has the above defined meaning, with benzoyl acetic acid esters of Formula XIII

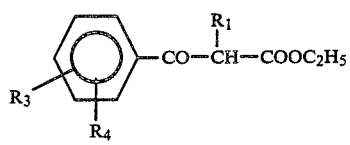

XIII in which $R_1$, $R_3$ and $R_4$ have the above defined meanings, or with phenyl propiolic acid esters of Formula XIV

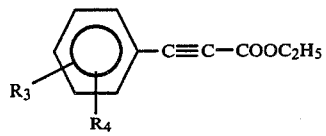

XIV in which $R_3$ and $R_4$ have the above defined meanings. The reaction takes place in an organic solvent which is inert under the reaction conditions, for example, a lower alkanol such as methanol or ethanol, an aromatic hydrocarbon, an open or cyclic ether or a halogenated hydrocarbon. If $R_2$ is lower alkyl, there is produced by the reaction a mixture of isomeric compounds in which $R_2$ is arranged in position 1 or 2. The ratio of 1-alkyl to 2-alkyl compounds may vary depending upon the nature of the starting materials and the solvent which is used. Isomeric mixtures of 1- and 2-alkyl compounds may be separated in a manner known as per se by fractional crystallization or by chromatography.

Acids and esters of Formula II are known, for example, from published European Patent Application No. 7019, or they may be produced according to methods known per se, for example, the methods described in the European Patent Application 7019.

Thus for the production of acids of Formula II, compounds of Formula VI may be reacted in a manner known per se with compounds of Formula XV

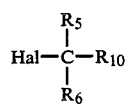

XV in which $R_5$, $R_6$ and Hal have the above defined meanings and $R_{10}$ is lower alkoxy carbonyl or cyano, to form (5-phenylpyrazole-3-oxy)-acetic acid esters and nitriles of Formula XVI

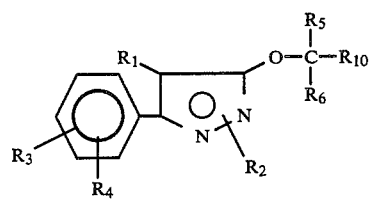

XVI in which $R_1$, $R_2$, $R_3$, $R_4$, $R_5$, $R_6$ and $R_{10}$ have the above defined meanings, and these may be subsequently hydrolysed. The reaction of the compounds of Formula VI with the compounds of Formula XV may be carried out according to methods known per se for the alkylation at the oxygen atom in position 3 of 5-phenylpyrazolin-3-ones under basic conditions, for example under the conditions indicated for method variant (c). The reaction may suitably be performed in dimethylformamide in the presence of potassium carbonate. In general, esters of Formula XV are used. If $R_5$ and $R_6$ are both hydrogen, nitriles of Formula XV prove to be advantageous. Insofar as the phenyl ring possesses a free hydroxy substituent, it is desirable to provide it prior to the reaction, in a manner known per se, with a protective group which is easily removable afterward under conditions under which the ether group in position 3 of the pyrazole structure and the amide group in the side chain of the compounds of Formula I are not affected.

If desired, in compounds of Formula XVI in which R₂ is hydrogen, an alkyl group R₂ may be introduced in a manner known per se through alkylation under basic conditions.

Compounds of Formula XVI may be hydrolysed in a manner known per se to form the corresponding acids of Formula II and these may be converted in a manner known per se into further reactive acid derivatives. The hydrolysis preferably takes place under alkaline conditions, for example by treatment with aqueous alkali metal hydroxide solution, optionally in the presence of an organic solvent which is miscible with water. The conversion of the free acids into reactive acid derivatives likewise takes place in a manner known per se. Thus acid halides of Formula II, for example may be obtained by reaction of the acids with an inorganic acid halide, for example thionyl chloride. Optionally the reaction may be carried out in the presence of pyridine or another tertiary organic base. Mixed acid anhydrides may be obtained for example by reaction of the acid with an equivalent quantity of another acid chloride, for example a sulphonic acid chloride, such as methane sulphonic acid chloride, in the presence of an acid-binding agent, preferably a tertiary organic base, such as triethyl amine.

Compounds of Formula II in which R₂ is hydrogen may be partially condensed during the methods of preparation described above to form the corresponding cyclic compounds of Formula III, so that the resulting compounds of Formula II may contain varying quantities of compounds of Formula III as a by-product depending upon the reaction conditions. As compounds of Formulae II and III may be further reacted in the same manner with an amine, the separating of any mixtures of compounds of Formula II and III into the individual compounds is unnecessary.

Pure compounds of Formula III may be obtained by the cyclizing condensation of the corresponding reactive acid derivatives of Formula II, particularly of mixed anhydrides of Formula II. The condensation takes place, for example, when the solution of a mixed anhydride of Formula II is left to stand at ambient temperature in an inert organic solvent, e.g., a halogenated hydrocarbon such as methylene chloride.

Compounds of the general Formula IV may be obtained in a manner known per se from compounds of the general Formula II, by reacting them with amino alcohols of Formula X

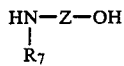   X in which R₇ has the above defined meaning, and subsequently converting the terminal hydroxy group in the side chain in the 3-position of the resulting product, in a manner known per se, into an aminolytically replaceable group X¹. The reaction of the compounds of Formula II with the compounds of Formula X may take place under conditions which are conventional for amide formation, for example the conditions described above for the reaction of compounds of Formula II with compounds of Formula VIII. In the reaction, the desired amide formation predominates. The terminal hydroxy group in the lateral chain of the resulting amide may be converted in a manner known per se into aminolytically replaceable group, for example with a conventional halogenating agent, such as for example thionyl chloride, phosphorus oxychloride or phosphorus tribromide, in order to obtain a compound of Formula IV, in which X¹ is halogen. Alternatively, the terminal hydroxy group may be esterified according to methods known per se, for example, reacted with a corresponding acid halide, in order to obtain compounds of Formula IV, in which X¹ is a reactive acid radical, particularly one of the above-mentioned sulphonic acid radicals. In these reactions, the terminal primary hydroxy group reacts predominantly before any secondary hydroxy group possibly contained in the substituent Z. For the production of compounds of Formula IV, in which X¹ is halogen, the compounds of Formula II may also be reacted directly with the corresponding haloalkylamines.

Compounds of Formula VII may be produced in a manner known per se by the reaction of corresponding -halocarboxylic acids or their reactive derivatives with diamines of Formula VIII under conventional conditions for amide formation.

Compounds of Formula IX may be obtained by reaction compounds of Formula II, particularly acid chlorides of Formula II, with amines of Formula XI

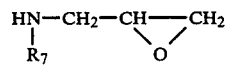   XI in which R₇ has the above defined meaning, in a manner known per se.

The compounds of Formula I and their pharmacologically acceptable acid addition salts have interesting pharmacological properties, particularly heart rhythmizing effects. The new compounds are distinguished by marked antiarrhythmic effects with a favourable activity profile and good physiological compatibility. In particular, the compounds display the property of raising the electrical stimulus threshold for eliciting rhythm disorders in the heart.

The doses to be used vary, of course, depending upon the nature of the compound administered, the manner of administration and the condition which is to be treated. In general, however, satisfactory results are obtained in tests on animals with doses of from 0.01 to 100 mg/kg body weight. Determination of the specific dose to be used in a given case is within the skill of the art.

The antiarrhythmic effects of the compounds can be shown in pharmacological test methods in animals.

1. Determination of protection from chloroform-induced ventricular fibrillation in mice The effect of the compounds on the ventricular fibrillation in mice brought about through chloroform inhalation leading to rapid respiratory arrest is determined according to Lawson's method (J. Pharmacol. Exp. Ther. 160, 22–23).

In this test arrangement, the minimal toxic dose can also be determined at the same time. The test substances in 0.9% NaCl solution are administered i.p. to female mice with a body weight of from 17 to 24 g. The animals are kept individually in glass beakers, where they are observed for possible toxic symptoms. Ten minutes after administration of the test substances, the animals are transferred to covered 300 ml glass beakers which contain a swab of cotton wool soaked with approximately 20 ml chloroform. Immediately after respiratory arrest has occurred, the animals are removed from the glass beaker and heart rhythm and rate are observed. The percentage of animals is determined, which are protected from chamber fibrillation by the dose of test substance which has been administered.

2. Determination of the electrical fibrillation threshold of the right ventricle in the heart of a guinea-pig The capability of the substances to raise the electrical stimulus threshold is determined on male albino Pirbright-white guinea-pigs with a body weight of from 250 to 450 g. The animals are narcotised by i.p. application of 1.50 g/kg urethane and are placed in a supine position on a thermal bench which is provided with a thermostat. The test substances are administered via a cannula connected into a vein. Each animal receives a series of increasing doses. The electrocardiogram is taken with a bipolar conductance (subcutaneous needle electrodes on both sides of the thorax) and is observed on an oscilloscope. Via a bipolar suction electrode which is introduced into the right ventricle through the vena jugularis, an intracardial stimulation is produced through a series of rectangular impulses (duration 1 ms, frequency 50 Hz, using a stimulator manufactured by the firm Hugo Sachs Elektronik). The current intensity is increased within 5 to 15 seconds up to occurrence of chamber fibrillation. The current intensity (in $\mu A$), at which chamber fibrillation is observed, is defined as the fibrillation threshold of the right ventricle. The fibrillation threshold of the individual animals is measured before application of the first dose and after each further dose of the test substance which is administered. The dose which on average causes an increase in the fibrillation threshold by 50% is defined as $ED_{150\%}$.

The results obtained by the test methods described above are shown in the following table. The Example numbers given for the compounds of Formula I refer to the preparation Examples which follow.

| Example No. | Minimal toxic dose mg/kg mouse i.p. | Inhibiting effect with respect to chloroform-induced chamber fibrillation in mice dose mg/kg | Inhibiting effect with respect to chloroform-induced chamber fibrillation in mice % protected animals | Increase of electrical stimulus threshold in the guinea-pig ED 150% i.v. $\mu$mol/kg |
|---|---|---|---|---|
| 1 | 200 | 25 | 100 | 1.4 |
| 3 | 200 | 25 | 67 | 0.42 |
| 9 | 200 | 50 | 33 | 2.6 |
| 16 | 200 | 50 | 100 | 3.0 |
| 18 | 100 | 10 | 100 | 0.78 |
| 25 | | | | 1.2 |
| 27 | | | | 1.5 |
| 28 | | | | 2.0 |
| 30 | 200 | 25 | 67 | 1.9 |
| 31 | 100 | 25 | 67 | 1.1 |
| 38 | 200 | 50 | 100 | 3.0 |
| 40 | 100 | 25 | 100 | 0.75 |
| 41 | 200 | 25 | 100 | 1.5 |
| 55 | >200 | 100 | 100 | 2.2 |
| 56 | | | | 2.6 |
| 64 | >200 | 100 | 100 | 1.7 |
| 59 | 200 | 50 | 100 | 2.6 |
| 68 | | | | 2.7 |

Because of their effects described above, the compounds of formula I and their pharmacologically acceptable acid addition salts are useful as medicaments for the treatment and prophylaxis of heart rhythm disorders. They may be administered by conventional enternal and parenteral techniques.

The compounds of Formula I and their physiologically compatible acid addition salts may be compounded, as medicines, with conventional pharmaceutical adjuvant substances in pharmaceutical preparations such as, for example, tablets, capsules, suppositories or solutions. These pharmaceutical preparation may be produced according to methods known per se using conventional solid carrier substances such as for example, lactose, starch or talcum, or liquid diluents such as for example water, fatty oils or liquid paraffins.

The invention will now be illustrated by the following non-limiting Examples which describe in further detail the production of new compounds of Formula I.

The structures of the new compounds were confirmed by spectroscopic examinations, in particular by analysis of the NMR-, mass-, IR- and/or UV- spectra.

EXAMPLE 1

3-[2-(3-diethylaminopropylaminocarbonyl)-propyl-2-oxy]-5-phenylpyrazole (A) 6.2 ml benzoyl acetic acid ethyl ester were mixed with 3.7 ml ethanol. 3.3 ml 80% hydrazine hydrate were added to the solution dropwise under ice cooling and the reaction mixture was left to stand for 12 hours. The precipitated 5-phenylpyrazolin-3-one was then filtered off and first washed with a little ethanol and then with diethyl ether. Melting point 236° to 240° C.; yield 5.5 g.

(B) 5 g 5-phenylpyrazolin-3-one were dissolved in 50 ml dimethyl formamide. 1.5 g of an approximately 50% oily sodium hydride preparation are added to the solution in portions. 15 minutes later, 5.7 ml 2-bromo-2-methylpropionic acid ethyl ester are added dropwise and the reaction mixture is stirred for 24 hours at a temperature of 80° C. The solvent was then evaporated under reduced pressure and the remaining residue was suspended in methylene chloride. After filtering off the precipitated sodium bromide crystals, the solution was washed with water and the aqueous washing waters are extracted once again with methylene chloride. The combined methylene chloride phases were dried over magnesium sulphate and concentrated. The crude product which was obtained was purified by column chromatography over silica gel using hexane/ether mixtures as elution agent. 4.9 g crystalline 3-(2-ethoxycarbonylpropyl-2-oxy)-5-phenylpyrazole were obtained. Melting point 79° C.

(C) 42 g 3-(2-ethoxycarbonylpropyl-2-oxy)-5-phenylpyrazole were dissolved in 200 ml ethanol, the solution was mixed with 103 ml 20% sodium hydroxide and the reaction mixture was heated under reflux to complete the reaction. The ethanol was largely distilled off and the remaining aqueous reaction mixture was acidified under ice cooling with 20% hydrochloric acid until the pH was 1. The precipitated 3-(2-hydroxycarbonylpropyl-2-oxy)-5-phenylpyrazole was filtered off. Melting point 152° to 155° C.; yield: 36.5 g.

(D) 493 mg 3-(2-hydroxycarbonylpropyl-2-oxy)-5-phenylpyrazole were suspended in 4 ml dry methylene chloride and mixed with 0.55 ml triethylamine. After 10 minutes the reaction mixture was cooled to −30° C. bath temperature, and in order to form a mixed anhydride, 0.16 ml methane sulphonic acid chloride was added dropwise and the mixture was stirred for a further hour at −30° C. The reaction mixture containing the resulting 2-methyl-2-[(5-phenylpyrazol-3yl)-oxy]-propionic acid methane sulphonic acid anhydride was immediately used in the following reaction.

(E) A spatula tip of 4-pyrrolidinopyridine was added to the reaction mixture produced under (D) and containing the mixed anhydride, and subsequently 0.32 ml 3-diethylaminopropylamine was added dropwise and the reaction mixture was slowly heated to ambient temperature and stirred for a further 2.5 hours. Then it was mixed with 5 ml methylene chloride and washed twice with dilute sodium carbonate solution. The organic phase was separated off, dried and concentrated. 649 mg of the title compound remained as an oily base (IR spectrum (as film): 3220 cm$^{-1}$, 1650 cm$^{-1}$, 1530 cm$^{-1}$). dissolved in acetone and converted into its hydrogen maleinate salt through the addition of a solution of 232 mg maleic acid in acetone. 644.5 mg 3-[2-(3-diethylaminopropylaminocarbonyl)-propyl-2-oxy]-5-phenyl-pyrazole-hydrogen maleinate were obtained; melting point 135° C.

EXAMPLE 2

3-[2-(3-diethylaminopropylaminocarbonyl)-propyl-2-oxy]-5-phenylpyrazole 0.32 ml 3-diethylaminopropylamine was added dropwise to a reaction mixture produced in an analogous manner to Example 1D and containing the mixed anhydride of 493 mg 3-[2-hydroxycarbonylpropyl-2-oxy]-5-phenylpyrazole and methane sulphonic acid, and the reaction mixture was slowly heated to ambient temperature and stirred for a further 2.5 hours. Then working up was carried out, as described in Example 1E. 515 mg of the title compound are obtained as an oily base. This was converted into its hydrogen maleinate as described in Example 1E. Melting point 135° C.

EXAMPLE 3

3-[2-(3-diethylamino-2-hydroxypropylaminocarbonyl)-propyl-2-oxy]-5-phenylpyrazole (A) 4.7 g 5-phenylpyrazolin-3-one and 4.1 g anhydrous potassium carbonate were suspended in 60 ml dimethyl formamide. The suspension was heated for approximately 10 minutes to 100° C., then cooled to 60° C. and mixed dropwise with 4.8 ml 2-bromo-2-methyl propionic acid ethyl ester. The mixture was stirred for 4 hours at 100° C. and subsequently the solvent was evaporated under reduced pressure and the residue was dissolved in 150 ml water. The aqueous solution was extracted twice with 150 ml diethyl ether in each case and the organic phase was dried over magnesium sulphate and concentrated; 6.9 g crude 3-(2-etoxycarbonylpropyl-2-oxy)-5-phenylpyrazole were obtained as an oil. This was crystallized from ethyl acetate; melting point 78.5° C. Subsequently the product was hydrolysed to 3-(2-hydroxycarbonylpropyl-2-oxy)-5-phenylpyrazole as described in Example 1C.

(B) 9.85 g 3-(2-hydroxycarbonylpropyl-2-oxy)-5-phenylpyrazole were reacted according to the method described in Example 1D with methane sulphonic acid chloride to form the mixed anhydride and this was reacted in situ with 3-diethylamino-2-hydroxypropylamine in an analogous manner to Example 1E. The reaction was worked up as described in Example 1E, and the resulting crude produce was chromatographed for further purification on a silica gel column using an ether/methanol mixture as elution agent. 10.5 g of the title compound were obtained as an oily base. This was dissolved in acetone and converted into its hydrogen maleinate salt through the addition of a solution of 3.25 g maleic acid in acetone. 10.6 g 3-[3-diethylamino-2-hydroxypropylaminocarbonylpropyl-2-oxy]-5-phenyl-pyrazole hydrogen maleinate were obtained; melting point 160°.

EXAMPLE 4

3-(2-aminoethylaminocarbonylpropyl-2-oxy)-5-phenyl-pyrazole 8.6 g 3-(2-hydroxycarbonylpropyl-2-oxy)-5-phenyl-pyrazole were dissolved in 60 ml methylene chloride and mixed with 9.7 ml triethylamine. After 10 minutes, the mixture was cooled to −30° C. bath temperature, and the mixture was mixed dropwise with 2.74 ml methane sulphonic acid chloride and stirred for a further hour at −30° C. The solution containing the resulting mixed anhydride was transferred into a dropping funnel kept at a temperature of −30° C. and was added dropwise into 45 ml ethylene diamine over a period of 1.5 hours. Subsequently the mixture was stirred for a further hour at ambient temperature to complete the reaction. The reaction mixture was then diluted with methylene chloride and washed with 20% sodium hydroxide solution. The organic phase was dried and evaporated. The remaining crude produce was purified by chromatography on aluminum oxide using methylene chloride/methanol as the elution agent. For conversion into its hydrogen maleinate, the chromatographically purified title compound was dissolved in acetone and mixed with a solution of 1.57 g maleic acid in acetone, and the solution was evaporated. The residue was taken up with water, the aqueous phase was extracted twice with ether and subsequently made alkaline by the addition of sodium carbonate solution, and the title base, released again from the maleinate, was extracted with ether. On evaporation of the ether extract 1.7 g of the title compound were obtained and dissolved together with 1.1 g maleic acid in isopropanol. The solution was added dropwise into ether, whereby the 3-(2-aminoethylaminocarbonylpropyl-2-oxy)-5-phenylpyrazole hydrogen maleinate precipitated out. It was filtered off and washed with ether. Melting point 128° to 135° C.; yield 1.3 g.

EXAMPLE 5

3-diethylaminoethylaminocarbonylmethoxy)-5-phenyl-pyrazole (A) In an analogous manner to the method described in Example 1B, 40 g 5-phenylpyrazolin-3-one in 120 ml dimethyl formamide were first deprotonated by reaction with 5.6 g of an 80% oily sodium hydride preparation and subsequently reacted with 11 ml chloroacetonitrile to form 3-cyanomethoxy-5-phenylpyrazole. Melting point: 143° C.

(B) 25.2 g 3-cyanomethoxy-5-phenylpyrazole were dissolved in 200 ml ethanol and mixed with 50 ml 20% sodium hydroxide solution. The reaction mixture was heated for one hour at reflux. After cooling, the mixture was acidified with 20% aqueous hydrochloric acid until the pH was 1. The precipitated 3-hydroxycarbonylmethoxy-5-phenylpyrazole was filtered off. Melting point: 193° C.; yield 22.3 g.

(C) 4.36 g 3-hydroxycarbonylmethoxy-5-phenylpyrazole were converted into the mixed acid anhydride by reaction with methane sulphonic acid chloride, and this was reacted in situ with 2-diethylaminoethylamine in accordance with the method described in Example 1D and E. The reaction mixture was worked up as described in Example 1E. The resulting 3-(diethylaminoethylaminocarbonylmethoxy)-5-phenylpyrazole was crystallized from ethyl acetate. Melting point 100 to 101° C.; yeild 4.6 g.

EXAMPLE 6

3-(2-morpholinoethylaminocarbonylmethoxy)-5-phenyl-pyrazole 1.33 ml N-(2-aminoethyl)-morpholine, 2.2 g 3-hydroxycarbonylmethoxy-5-phenylpyrazole and 4.3 ml triethylamine were added in this order to 3.06 g 1-methyl-2-chloropyridinum iodide in methylene chloride. The reaction mixture was then heated to boiling for 3 hours under reflux. After cooling and washing with aqueous sodium hydroxide solution, the organic phase was evaporated, and the crude product obtained was purified chromatographically. 2.3 g 3-(2-morpholinoethylaminocarbonylmethoxy)-5-phenyl-pyrazole were obtained as an oily base. IR-spectrum (as film): 3205 cm$^{-1}$, 1660 cm$^{-1}$.

EXAMPLE 7

3-[2-(3-diethylaminopropylaminocarbonyl)-propyl-2-oxy]-5-(3,4-dichlorophenyl)-pyrazole 13.7 g 3-(2-ethoxycarbonylpropyl-2-oxy)-5-(3,4-dichlorophenyl)-pyrazole were added to 30 ml 3-diethylaminopropylamine and the reaction mixture was heated under nitrogen for 18 hours at 180° C. On completion of the reaction, excess amine was distilled off in vacuum. Then the crude title compound which was obtained was dried in a desiccator over concentrated sulphuric acid. 16.2 g 3-[2-(3-diethylaminopropylaminocarbonyl)-propyl-2-oxy]-5-(3,4-dichlorophenyl)-pyrazole remained as an oily base. For further purification, the compound was dissolved in ether, and the etheral solution was filtered over silica gel. IR-spectrum (as film): 322 cm$^{-1}$, 1645 cm$^{-1}$, 1530 cm$^{-1}$.

EXAMPLE 8

3-[2-(3-morpholinopropylaminocarbonyl)-propyl-2-oxy]-5-phenylpyrazole 9 g 3-(2-hydroxycarbonylpropyl-2-oxy)-5-phenyl-pyrazole were dissolved in methylene chloride and 5.6 ml triethylamine were added dropwise under ice cooling. After stirring for 30 minutes, 3.6 ml ethyl choroformate were added dropwise and the reaction mixture was stirred for a further hour at ambient temperature. The reaction mixture containing the resulting 3-(2-ethoxycarbonyloxycarbonylpropyl-2-oxy)-5-phenyl-pyrazole was then added dropwise under ice cooling to a solution of 8 ml N-(3-aminopropyl)-morpholine in methylene chloride. The mixture was stirred for a further hour under ice cooling and for a further hour at ambient temperature, and was then washed with dilute sodium hydroxide solution. The organic phase was dried and evaporated, and the residue was dissolved in 75 ml ethanol. 35 ml 20% sodium hydroxide were added, and the mixture was heated for 3 hours under reflux. It was then reduced to half the volume, diluted with water and extracted with methylene chloride. The crude product obtained from the methylene chloride phase was purified by chromatography on silica gel using an ether/methanol mixture. 5.9 g 3[2-(3-morpholinopropylaminocarbonyl)-propyl-2-oxy]-5-phenyl-pyrazole were obtained as an oily base. IR-spectrum (as film): ~3240 cm$^{-1}$, 1650 cm$^{-1}$, 1530 cm$^{-1}$.

EXAMPLE 9

3-[2-(3-diethylaminopropylaminocarbonyl)-propyl-2-oxy]-1-methyl-5-phenylpyrazole (A) 20.5 g methyl propionate were dissolved in 150 ml toluene and 6.7 ml methyl hydrazine were added to the solution under ice cooling. After standing for 12 hours, the solution was evaporated. The residue was a mixture of 1-methyl-5-phenylpyrazolin-3-one and 2-methyl-5-phenylpyrazolin-3-one. This crude isomeric mixture was chromatographed on silica gel. Ether was used as elution agent, to which increasing quantities of methanol were added. From the eluate the non-polar 1-methyl-5-phenylpyrazolin-3-one was isolated. Melting point: 160°-161° C.; yield 6.3 g.

(B) 4.5 g 1-methyl-5-phenylpyrazolin-3-one were reacted, as described in Example 3A, to form 3-(2-ethoxycarbonylpropyl-2-oxy)-1-methyl-5-phenyl-pyrazole, and this was further hydrolyzed without purifying to form 3-(2-hydroxycarbonylpropyl-2-oxy)-1-methyl-5-phenylpyrazole.

(C) The crude 3-(2-hydroxycarbonylpropyl-2-oxy)-1-methyl-5-phenylpyrazole obtained above was converted as described in Example 1D by reaction with methane sulphonic acid chloride into the mixed anhydride, and this was reacted with 3-diethylaminopropylamine. The reaction mixture was worked up as described in Example 1E, and the title compound was isolated as an oily base. IR-spectrum (as film): ~3340 cm$^{-1}$, 1668 cm$^{-1}$, 1545 cm$^{-1}$. The title compound was then converted into its hydrogen maleinate as described in Example 1E. 3.27 g 3-[2-(3-diethylaminopropylaminocarbonyl)-propyl-2-oxy]-1-methyl-5-phenylpyrazole-hydrogen maleinate were obtained as an oil.

EXAMPLE 10

3-[2-(3-diethylaminopropylaminocarbonyl)-propyl-2-oxy]-5-phenylpyrazole (A) 2.3 g 3-(2-hydroxycarbonylpropyl-3-oxy)-5-phenylpyrazole (prepared as described in Example 1C) were suspended in 50 ml dry methylene chloride and mixed with 2.6 ml triethylamine. After 10 minutes the reaction mixture was cooled to −30° C. bath temperature, and, in order to form a mixed anhydride according to the method described in Example 1D, was mixed dropwise with 0.72 ml methane sulphonic acid chloride and stirred for a further hour at −30° C. The reaction solution containing the mixed anhydride was then slowly heated to ambient temperature for the cyclizing condensation of the mixed anhydride to the corresponding 2,2-dimethyl-6-phenyl-pyrazolo-[5,1-b]-oxazolin-3-one and was stirred at ambient temperature until the reaction was complete. Then the reaction mixture was washed with sodium carbonate solution the organic phase was separated off, dried and partly evaporated. The resulting 2,2-dimethyl-6-phenyl-pyrazolo-[5,1-b]-oxazolin-3-one was recrystallized from a mixture of ethyl acetate and diethyl ether. Melting point 110° C.

(B) 230 mg 2,2-dimethyl-6-phenyl-pyrazolo-[5,1-b]-oxazolin-3-one and 0.16 ml 3-diethylamino-propylamine were dissolved in 1 ml dry tetrahydrofuran, and the solution was stirred under a nitrogen atmosphere at ambient temperature for approximately 50 hours. The solvent was evaporated under vacuum, and the residue was dissolved in diethyl ether. The solution was washed with concentrated sodium carbonate solution, and the organic phase was separated off, dried and evaporated.

360 mg 3-[2-(3-diethylamino-propylaminocarbonyl)-propyl-2-oxy]-5-phenylpyrazole were obtained as an oily base. This was converted into its hydrogen maleinate as described in Example 1E. Melting point 135° C.

EXAMPLE 11

3-[2-(3-diethylaminopropylaminocarbonyl)-propyl-2-oxy]-5-phenylpyrazole 230 mg 2,2-dimethyl-6-phenyl-pyrazolo-[5,1-b]-oxazolin-3-one (prepared as in Example 10A) were dissolved in approximately 2 ml 3-diethylaminopropylamine under nitrogen, and the solution was allowed to stand for 2 hours at ambient temperature. Then the excess amine was distilled off in vacuum. The remaining crude title compound was dried in a desicator over concentrated sulphuric acid to remove basic impurities. 360 mg 3-[2-(3-diethylaminopropylaminocarbonyl)-propyl-2-oxy]-5-phenylpyrazole were obtained as an oily base. This was converted into its hydrogen maleinate as described in Example 1E. Melting point; 135° C.

EXAMPLE 12

3-[2-(2-morpholinoethylaminocarbonyl)-propyl-2-oxy]-2-methyl-5-phenylpyrazole (A) 5 g 3-(2-hydroxycarbonylpropyl-2-oxy)-2-methyl-5-phenylpyrazole were suspended in 40 ml dry methylene chloride and mixed with 8.3 ml triethylamine. After 10 minutes 1.48 ml methane sulphonic acid chloride were added dropwise, and the reaction mixture was stirred for a further 30 minutes. Then a spatula tip of 4-pyrrolidinopyridine was added to the reaction mixture containing the mixed anhydride, and subsequently 3.9 g 2-bromoethylamine hydrobromide were added in portions within 30 minutes. The reaction mixture was allowed to stand for 3 hours and was then washed first with aqueous citric acid solution and thereafter with sodium carbonate solution. The organic phase was dried and partly evaporated. As a residue 3.8 g 3-[2-(2-bromoethylaminocarbonyl)-propyl-2-oxy]-2-methyl-5-phenylpyrazole were obtained. Melting point 130° C.

(B) 3.8 g 3-[2-(2-bromoethylaminocarbonyl)-propyl-2-oxy]-2-methyl-5-phenylpyrazole were dissolved in a little ethanol, and the solution was added dropwise over a period of 2 hours into 100 ml boiling morpholine. The reaction mixture was heated at reflux for a further 30 minutes and then concentrated in vacuum. The residue was taken up in methylene chloride and extracted with aqueous citric acid solution. The aqueous phase was separated, made alkaline by the addition of sodium carbonate solution and extracted with ether. The other phase was separated and evaporated. The remaining residue was dried in a desiccator over sulphuric acid. The crude title compound thus obtained was purified through chromatography on silica gel. 2.8 g 3-[2-(2-morpholinoethylaminocarbonyl)-propyl-2-oxy]-2-methyl-5-phenylpyrazole were obtained. Melting point 105° C. IR-spectrum (in KBr): ~3340 cm$^{-1}$ 1670 cm$^{-1}$, 1545 $^{-1}$.

EXAMPLE 13

3-[2-(3-diethylaminopropylaminocarbonyl)-propyl-2-oxy]-5-phenylpyrazole (A) 3.4 g 2-bromo-2-methylpropionic acid were added to 30 ml dry methylene chloride and mixed with 5.4 ml triethylamine. After 10 minutes the reaction mixture was cooled to −30° C. bath temperature, 1.4 ml methane sulphonic acid chloride were added dropwise, and the mixture was stirred for a further hour at −30° C. to form a mixed anhydride. Then a spatula tip of 4-pyrrolidinopyridine was added, and 3.1 ml of 3-diethylaminopropylamine were added dropwise, and the reaction mixture was slowly heated to ambient temperature and stirred at ambient temperature for a further 2.5 hours. Then 40 ml methylene chloride were added, and the mixture was washed twice with dilute sodium carbonate solution. The organic phase was separated, dried and concentrated. 3 g N-(3-diethylaminopropyl)-2-bromo-2-methylpropionic acid amide were obtained as an oily base. IR-spectrum (as film): 3310 cm$^{-1}$, 1660 cm$^{-1}$, 1530 cm$^{-1}$.

(B) 1.6 g 5-phenylpyrazolin-3-one and 2 g anhydrous potassium carbonate were suspended in 20 ml dimethylformamide. The suspension was heated for 10 minutes to 100° C. Then it was cooled to 60° C., and a solution of 3 g N-(3-diethylaminopropyl)-2-bromo-2-methylpropionic acid amide in 10 ml dimethyl formamide was added dropwise to the mixture. The reaction mixture was stirred for 4 hours at 100° C. Then the solvent was evaporated under reduced pressure, and the residue was dissolved in 50 ml water. The aqueous solution was extracted twice with 50 ml diethyl ether in each case. The combined ether extracts were dried over magnesium sulphate and concentrated. 0.9 g 3-[2-(3-diethylaminopropylaminocarbonyl)-propyl-2-oxy]-5-phenylpyrazole were obtained as an oily base. IR-spectrum (as film): 3220 cm$^{-1}$, 1650 cm$^{-1}$, 1530 cm$^{-1}$. The base was converted into its hydrogen maleinate as described in Example 1E. Melting point 135° C.

EXAMPLE 14

3-[2-(3-diethylaminopropylaminocarbonyl)-propyl-2-oxy]-5-(4-hydroxyphenyl)-pyrazole 160 mg 3-[2-(3-diethylaminopropylaminocarbonyl)-propyl-2-oxy]-5-(4-methoxyphenyl)-pyrazole were mixed with 0.32 ml acetic anhydride and 0.7 ml 57% aqueous hydroiodic acid. The mixture was heated for one hour under reflux and was then carefully added into ice-cold sodium carbonate solution and extracted exhaustively with diethyl ether. The ether extract was dried over magnesium sulphate and evaporated. The remaining crude title compound was purified by chromatography on silica gel (elution agent: ethyl acetate containing 15% triethylamine). 15 mg 3-[2-(3-diethylaminopropylaminocarbonyl)-propyl-2-oxy]-5-(4-hydroxy-phenyl)-pyrazole were obtained. IR-spectrum (as film): 3220 cm$^{-1}$, 1655 cm$^{-1}$, ~1530 cm$^{-1}$.

The compounds of Formula I listed in the following Table can also be prepared according to the methods described in the foregoing examples. The IR-bands indicated in cm$^{-1}$ in the Table are the most characteristic bands of the IR-spectra of the respective free bases (as film unless indicated otherwise).

| Example No. | R₁ | R₂ | R₃ | R₄ | R₅ | R₆ | R₇ | Z | R₈ | R₉ | Remarks |
|---|---|---|---|---|---|---|---|---|---|---|---|
| 15 | H | 2-CH₃ | H | H | CH₃ | CH₃ | H | CH₂—CHOH—CH₂ | —(CH₂)₅— | | H—ma,oil; B,oil IR: ~3360,1665,1545 |
| 16 | H | 2-CH₃ | H | H | CH₃ | CH₃ | H | n-C₃H₆ | C₂H₅ | C₂H₅ | H—ma,oil; B,oil IR: 3330,1660,1540 |
| 17 | H | H | H | H | H | H | H | C₂H₄ | CH₃ | CH₃ | B,MP 123° C. |
| 18 | CH₃ | H | H | H | CH₃ | CH₃ | H | C₂H₄ | C₂H₅ | C₂H₅ | H—ma,oil; B,oil IR: ~3230,1655,1518 |
| 19 | H | H | H | H | CH₃ | CH₃ | H | C₂H₄ | C₂H₄—O—C₂H₄ | | B,MP 120° C. |
| 20 | H | H | H | H | H | H | CH₃ | C₂H₄ | CH₃ | CH₃ | H—ma,MP 130° C. |
| 21 | H | H | H | H | CH₃ | CH₃ | CH₃ | C₂H₄ | CH₃ | CH₃ | B,oil IR:~3220,~1625 |
| 22 | H | H | H | H | CH₃ | CH₃ | C₂H₅ | C₂H₄ | C₂H₅ | C₂H₅ | H—fu,oil; B,oil IR: ~3230,~1630 |
| 23 | H | H | H | H | CH₃ | CH₃ | H | C₂H₄ | H | CH(CH₃)₂ | B,MP 133° C. |
| 24 | H | H | H | H | H | H | H | n-C₃H₆ | C₂H₅ | C₂H₅ | B,MP 74–75° C. |
| 25 | CH₃ | H | H | H | CH₃ | CH₃ | H | n-C₃H₆ | C₂H₅ | C₂H₅ | H—ma, MP 90–95° C. |
| 26 | H | H | H | H | CH₃ | CH₃ | H | n-C₃H₆ | n-C₄H₉ | n-C₄H₉ | B,oil IR: ~3220,~1655, ~1525 |
| 27 | H | H | H | H | CH₃ | CH₃ | H | n-C₃H₆ | —C(CH₃)—(CH₂)₄— | | H—ma,foam; B,oil IR: ~3210,~1650, 1525 |
| 28 | H | H | H | H | CH₃ | CH₃ | H | n-C₃H₆ | —(CH₂)₅— | | H—ma,oil B,oil IR: ~3200,~1655, 1525 |
| 29 | CH₃ | H | H | H | CH₃ | CH₃ | H | n-C₃H₆ | C₂H₄—O—C₂H₄ | | B,MP 124° C. |
| 30 | H | H | H | H | CH₃ | CH₃ | H | CH₂—CH₂—(1-CH₃—pyr-2) | | | H—ma,foam; B,oil IR: ~3210,~1660, 1530 |
| 31 | CH₃ | H | H | H | CH₃ | CH₃ | H | CH₂—CHOH—CH₂ | C₂H₅ | C₂H₅ | H—ma oil;B, MP. 108° C. |
| 32 | CH₃ | H | H | H | CH₃ | CH₃ | H | CH₂—CHOH—CH₂ | C₂H₄—O—C₂H₄ | | H—ma,foam; B; MP 148° C. |
| 33 | H | H | H | H | CH₃ | CH₃ | H | CH₂—CHOH—CH₂ | C₂H₄—O—C₂H₄ | | H—ma,foam; B,oil, IR: ~3250,1650, 1530 |
| 34 | H | H | 4-CH₃ | H | H | C₂H₅ | H | C₂H₄ | C₂H₅ | C₂H₅ | H—ma,oil; B,oil IR: ~3240,1658,1530 |
| 35 | H | H | 4-CH₃ | H | C₂H₅ | H | H | C₂H₄ | —(CH₂)₅— | | H—ma,foam B,oil IR: ~3240,1658, ~1530 |
| 36 | H | H | 4-CH₃ | H | C₂H₅ | H | H | C₂H₄ | C₂H₄—O—C₂H₄ | | H—ma,oil; B,oil IR: ~3230,1652, ~1530 |
| 37 | H | H | 4-CH₃ | H | CH₃ | CH₃ | H | n-C₃H₆ | C₂H₅ | C₂H₅ | H—ma,oil; B,oil IR: ~3220,1652, ~1530 |
| 38 | H | H | 4-CH₃ | H | H | C₂H₅ | H | n-C₃H₆ | C₂H₅ | C₂H₅ | H—ma,oil; B,oil IR: ~3220,1650, 1530 |
| 39 | H | H | 3-CF₃ | H | CH₃ | CH₃ | H | n-C₃H₆ | C₂H₅ | C₂H₅ | H—ma,MP 132° C. |
| 40 | H | H | 2-F | H | —(CH₂)₃— | | H | n-C₃H₆ | C₂H₅ | C₂H₅ | H—ma,MP 107° C. |
| 41 | H | H | 2-Cl | H | CH₃ | CH₃ | H | n-C₃H₆ | C₂H₅ | C₂H₅ | H—ma,oil; B,oil IR: ~3200,1650, 1525 |
| 42 | H | H | 4-Cl | H | H | C₂H₅ | H | C₂H₄ | C₂H₅ | C₂H₅ | H—ma,oil; B,oil IR: ~3220,1653, 1525 |
| 43 | H | H | 4-Cl | H | H | C₂H₅ | H | C₂H₄ | C₂H₄—O—C₂H₄ | | H—ma,foam; B,MP. 125–127° C. |
| 44 | H | H | 4-Cl | H | H | C₂H₅ | H | n-C₃H₆ | C₂H₅ | C₂H₅ | H—ma,oil,B, MP 119° C. |
| 45 | CH₃ | H | 4-Cl | H | CH₃ | CH₃ | H | n-C₃H₆ | C₂H₄—O—C₂H₄ | | H—ma,foam;B, MP 141° C. |
| 46 | CH₃ | H | 4-Cl | H | CH₃ | CH₃ | H | n-C₃H₆ | C₂H₅ | C₂H₅ | H—ma,foam,B,oil IR: ~3220,~1650, ~1525 |
| 47 | H | H | 4-Cl | H | H | C₂H₅ | H | C₂H₄ | —(CH₂)₅— | | B,foam IR*: 3210,1655,1530 |
| 48 | H | H | 4-Cl | H | H | C₂H₅ | H | C₂H₄ | —(CH₂)₄— | | B,MP 115° C. |
| 49 | H | H | 4-Br | H | CH₃ | CH₃ | H | C₂H₄ | C₂H₅ | C₂H₅ | H₂—ma,B, IR: 3230,1655,~1530 |
| 50 | H | H | 4-Br | H | CH₃ | CH₃ | H | n-C₃H₆ | C₂H₅ | C₂H₅ | H—ma,oil; B,oil IR: ~3200,~1650, ~1530 |
| 51 | H | H | 4-CH₃O | H | CH₃ | CH₃ | H | CH₂—CHOH—CH₂ | C₂H₅ | C₂H₅ | H—cit,foam; B,oil |

-continued

| Example No. | $R_1$ | $R_2$ | $R_3$ | $R_4$ | $R_5$ | $R_6$ | $R_7$ | Z | $R_8$ | $R_9$ | Remarks |
|---|---|---|---|---|---|---|---|---|---|---|---|
| 52 | H | H | 4-CH$_3$O | H | CH$_3$ | CH$_3$ | H | n-C$_3$H$_6$ | C$_2$H$_5$ | C$_2$H$_5$ | IR: ~3250,1655,1530 H—ma,oil; B,oil |
| 53 | H | H | 4-CH$_3$O | H | CH$_3$ | CH$_3$ | H | n-C$_3$H$_6$ | C$_2$H$_4$—O—C$_2$H$_4$ | | IR: ~3220,1650,1530 H—ma,oil; B,oil |
| 54 | H | H | 3,4-di-CH$_3$O | CH$_3$ | CH$_3$ | CH$_3$ | H | C$_2$H$_4$ | —(CH$_2$)$_4$— | | IR: ~3240,1650,1530 H—ma,MP 172° C. |
| 55 | H | H | 3,4-di-CH$_3$O | CH$_3$ | CH$_3$ | CH$_3$ | H | n-C$_3$H$_6$ | C$_2$H$_5$ | C$_2$H$_5$ | H—ma,oil; B,oil |
| 56 | H | H | —O—CH$_2$—O— | | CH$_3$ | CH$_3$ | H | n-C$_3$H$_6$ | C$_2$H$_5$ | C$_2$H$_5$ | IR: ~3220,1650 H—ma,oil; B,oil |
| 57 | CH$_3$ | H | H | H | CH$_3$ | CH$_3$ | H | C$_2$H$_4$ | —(CH$_2$)$_4$— | | IR: ~3210,1650,1530 H—ma,oil; B, MP 108° C. |
| 58 | H | H | H | H | n-C$_3$H$_7$ | H | H | CH$_2$—CHOH—CH$_2$ | C$_2$H$_5$ | C$_2$H$_5$ | H—ma,oil B,oil |
| 59 | H | H | H | H | CH$_3$ | CH$_3$ | H | n-C$_4$H$_8$ | C$_2$H$_5$ | C$_2$H$_5$ | IR: ~3240,1658,1530 H—ma,oil; B,oil |
| 60 | H | 1-C$_2$H$_5$ | H | H | CH$_3$ | CH$_3$ | H | n-C$_3$H$_6$ | C$_2$H$_5$ | C$_2$H$_5$ | IR: ~3210,1655,1530 H—ma,oil; B,foam |
| 61 | H | 1-C$_2$H$_5$ | H | H | CH$_3$ | CH$_3$ | H | C$_2$H$_4$ | C$_2$H$_5$ | C$_2$H$_5$ | IR: ~3430,1665,1535 H—ma,oil; B,oil |
| 62 | H | 1-CH$_2$—CH(CH$_3$)CH$_3$ | H | H | CH$_3$ | CH$_3$ | H | n-C$_3$H$_6$ | C$_2$H$_5$ | C$_2$H$_5$ | IR: ~3400,1670 H—fu,oil,B,oil IR: 3340,1668,530 |
| 63 | H | H | 4-NO$_2$ | H | CH$_3$ | CH$_3$ | H | n-C$_3$H$_6$ | C$_2$H$_5$ | C$_2$H$_5$ | H—ma,oil; B,oil IR: ~3210,1650,1515 |
| 64 | H | 2-CH$_3$ | H | H | CH$_3$ | CH$_3$ | H | CH$_2$—CHOH—CH$_2$ | C$_2$H$_5$ | C$_2$H$_5$ | H—ma-oil; B,oil IR: ~3340,~1670, 1545 |
| 65 | H | 2-CH$_3$ | H | H | CH$_3$ | CH$_3$ | H | CH$_2$—CHOH—CH$_2$ | —C$_2$H$_4$—O—C$_2$H$_4$ | | B,oil IR: ~3340,~1665, 1545 |
| 66 | CH$_3$ | 1-CH$_3$ | H | H | CH$_3$ | CH$_3$ | H | n-C$_3$H$_6$ | C$_2$H$_5$ | C$_2$H$_5$ | H—ma,oil; B,oil IR: 3350,1670,1520 |
| 67 | H | 2-C$_2$H$_5$ | H | H | CH$_3$ | CH$_3$ | H | n-C$_3$H$_6$ | C$_2$H$_5$ | C$_2$H$_5$ | H—fu,oil; B,oil IR: 3315,1665,1545 |
| 68 | H | 2-n-C$_3$H$_7$ | H | H | CH$_3$ | CH$_3$ | H | n-C$_3$H$_6$ | C$_2$H$_5$ | C$_2$H$_5$ | H—ma, MP 95-100° C. |
| 69 | H | 2-CH$_2$—CH(CH$_3$)CH$_3$ | H | H | CH$_3$ | CH$_3$ | H | n-C$_3$H$_6$ | C$_2$H$_5$ | C$_2$H$_5$ | H—ma, MP 105-115° C. |
| 70 | H | H | H | H | CH$_3$ | CH$_3$ | H | C$_2$H$_4$ | —(CH$_2$)$_5$— | | B,oil IR: 3200,1658,1520 |
| 71 | H | H | H | H | CH$_3$ | CH$_3$ | H | C$_2$H$_4$ | H | CH$_3$ | H—ma,foam B,oil IR: ~3220,1660,1530 |
| 72 | H | H | H | H | n-C$_3$H$_7$ | H | H | n-C$_3$H$_6$ | C$_2$H$_5$ | C$_2$H$_5$ | H—ma,oil; B,oil IR: ~3230,1655,1531 |
| 73 | H | H | H | H | CH$_3$ | CH$_3$ | H | n-C$_5$H$_{10}$ | C$_2$H$_5$ | C$_2$H$_5$ | H—ma,oil; B,oil IR: 3210,1655,1532 |

B = base, oil = oily; foam = foam resin; H—ma = hydrogen maleinate; H—trat = hydrogen tartrate; H—fu = hydrogen fumarate; H2—cit = dihydrogen citrate; * = in KBr; MP = melting point The invention is further illustrated by the following Example of a pharmaceutical composition.

EXAMPLE I

TABLETS

Tablets are produced with the following composition per tablet:
3-[2-(3-diethylaminopropylaminocarbonyl)-propyl-2-oxy]-5-phenylpyrazole-hydrogen maleinate: 15 mg
Maize starch: 60 mg
Lactose: 140 mg
Gelatine (as 10% solution): 6 mg.

The active substance, the maize starch and the lactose are thickened with the 10% gelatine solution. The paste is comminuted and the resulting granulate is deposited onto a suitable metal sheet and dried. The dried granulate is guided through a crushing machine and mixed in a mixer with the following further adjuvant substances:
Talcum: 5 mg
Magnesium stearate: 5 mg
Maize starch: 9 mg
and then compressed to 240 mg tablets.

The foregoing description has been set forth merely to illustrate the invention and is not intended to be limiting. Since modifications of the described embodiments incorporating the spirit and substance of the invention may occur to persons skilled in the art, the scope of the invention is to be limited solely with respect to the appended claims and equivalents.

What is claimed is:

1. A 3-aminocarbonylmethoxy-5-phenylpyrazole compound corresponding to the Formula I

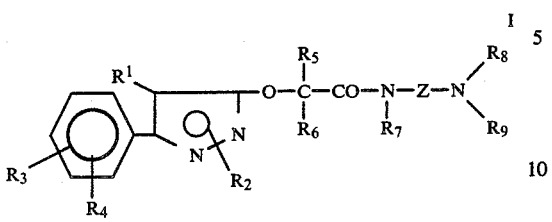

wherein
$R_1$ is hydrogen or lower alkyl,
$R_2$ is in position 1 or 2 on the pyrazole ring and is hydrogen or lower alkyl,
$R_3$ is hydrogen, halogen, lower alkyl or lower alkoxy and
$R_4$ is hydrogen, hydrogen, lower alkyl, lower alkoxy or if $R_3$ is hydrogen, $R_4$ may also be trifluoromethyl, nitro or hydroxy or
$R_3$ and $R_4$ are linked to adjacent carbon atoms and together represent an alkylene dioxy group with 1 or 2 carbon atoms,
$R_5$ is hydrogen or lower alkyl and
$R_6$ is hydrogen or methyl or
$R_5$ and $R_6$ together from an alkylene chain with 3 to 5 carbon atoms,
$R_7$ is hydrogen or lower alkyl,
Z is an alkylene chain with 2 to 5 carbon atoms or the 2-hydroxypropylene chain,
$R_8$ is hydrogen or lower alkyl and
$R_9$ is hydrogen or lower alkyl or
$R_8$ and $R_9$ together with the nitrogen atom to which they are linked represent a heterocyclic group corresponding to the Formula a:

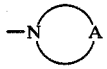

wherein A is an alkylene chain with 4 or 5 carbon atoms which chain may be substituted by 1 or 2 methyl groups, or A is the $-C_2H_4-O-C_2H_4-$ chain, or if Z is an alkylene chain, then
$R_8$ may be hydrogen or lower alkyl and
$R_9$ may be an alkylene chain, which together with the nitrogen atom to which it is linked and the carbon atom of the alkylene chain Z which is adjacent to this nitrogen atom, forms a 5- or 6-membered heterocycle, or a pharmaceutically acceptable acid addition salt thereof.

2. A 3-aminocarbonylmethoxy-5-phenylpyrazole compound according to claim 1, wherein
$R_1$ is hydrogen or alkyl with 1 or 2 carbon atoms and
$R_2$ is hydrogen or methyl.

3. A 3-aminocarbonylmethoxy-5-phenylpyrazole compound according to claim 1, wherein
$R_5$ and $R_6$ together have 3 carbon atoms.

4. A 3-aminocarbonylmethoxy-5-phenylpyrazole compound according to claim 1, wherein -
$R_5$ and $R_6$ are each methyl or $R_5$ is alkyl with 1 to 3 carbon atoms and $R_6$ is hydrogen.

5. A 3-aminocarbonylmethoxy-5-phenylpyrazole compound according to claim 1, wherein $R_8$ is hydrogen or alkyl with 1 or 2 carbon atoms and $R_9$ is hydrogen or alkyl with 1 or 2 carbon atoms; and $R_8$ and $R_9$ together with the nitrogen atom to which they are linked, represent a pyrrolidine, piperidine or morpholine ring; or
$R_8$ is hydrogen or methyl and $R_9$ together with the nitrogen atom and the carbon atom of the alkylene chain Z adjacent thereto represents a pyrrolidine ring.

6. A 3-aminocarbonylmethoxy-5-phenylpyrazole compound according to claim 1, wherein
$R_1$ is hydrogen or alkyl with 1 or 2 carbon atoms,
$R_2$ is hydrogen or methyl,
$R_3$ is hydrogen, halogen, methoxy or methyl,
$R_4$ is hydrogen, halogen, methoxy or methyl,
$R_5$ and $R_6$ are each methyl,
$R_7$ is hydrogen,
Z is an alkylene chain with 2 to 4 carbon atoms or the 2-hydroxypropylene chain, and
$R_8$ is hydrogen or alkyl with 1 or 2 carbon atoms and
$R_9$ is alkyl with 1 or 2 carbon atoms or
$R_8$ and $R_9$ together with the nitrogen atom to which they are linked form a pyrrolidine or piperidine ring.

7. A 3-aminocarbonylmethoxy-5-phenylpyrazole compound according to claim 6, wherein $R_1$ is hydrogen or methyl.

8. A 3-aminocarbonylmethoxy-5-phenylpyrazole compound according to claim 6, wherein Z is an alkylene chain with 3 or 4 carbon atoms or the 2-hydroxypropylene chain.

9. A 3-aminocarbonylmethoxy-5-phenylpyrazole compound according to claim 6, wherein $R_1$ is an alkyl group with 1 or 2 carbon atoms, and Z is an ethylene chain.

10. A 3-aminocarbonylmethoxy-5-phenylpyrazole compound according to claim 6, wherein $R_8$ and $R_9$ are each alkyl with 1 or 2 carbon atoms or $R_8$ and $R_9$ together with the nitrogen atom to which they are linked form a pyrrolidine or piperidine ring.

11. 3-[2-(3-diethylaminopropylaminocarbonyl)-propyl-2-oxy]5-phenylpyrazole according to claim 1 or a pharmaceutically acceptable acid addition salt thereof.

12. 3-[2-(3-diethylamino-2-hydroxypropylaminocarbonyl)-propyl-2-oxy]-5-phenylpyrazole according to claim 1 or a pharmaceutically acceptable acid addition salt thereof.

13. 3-[1-2-pyrrolidinoethylaminocarbonyl)-propyl-1-oxy]-5-(4-chlorophenyl)-pyrazole according to claim 1 or a pharmaceutically acceptable acid addition salt thereof.

14. An antianythmic pharmaceutical composition containing an antianythmic effective quantity of a 3-aminocarbonylmethoxy-5-phenylpyrazole compound according to claim 1 and at least one additional substance selected from the group consisting of conventional pharmaceutical adjuvants and carriers.

15. A compound corresponding to the Formula III

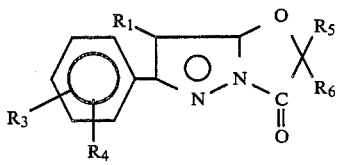

wherein
$R_1$ is hydrogen or lower alkyl, $R_3$ is hydrogen, halogen, lower alkyl or lower alkoxy and $R_4$ is hydrogen, halogen, lower alkyl, lower alkoxy or, if $R_3$ is hydrogen, $R_4$ may also be trifluormethyl, nitro or hydroxy or $R_3$ and $R_4$ are linked to two adjacent carbon atoms and together represent an alkylene dioxy group with 1 or 2 carbon atoms, $R_5$ is hydrogen or lower alkyl and $R_6$ is hydrogen or methyl or $R_5$ and $R_6$ together form an alkylene chain with 3-5 carbon atoms.

16. A compound corresponding to the Formula IV

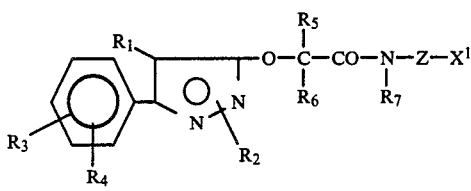

wherein $R_1$ is hydrogen or lower alkyl, $R_2$ is in position 1 or 2 on the pyrazole ring and is hydrogen or lower alkyl, $R_3$ is hydrogen, halogen, lower alkyl or lower alkoxy and $R_4$ is hydrogen, halogen, lower alkyl, lower alkoxy or, if $R_3$ is hydrogen, $R_4$ may also be trifluoromethyl, nitro or hydroxy or $R_3$ and $R_4$ are linked to adjacent carbon atoms and together represent an alkylene group with 1 or 2 carbon atoms, $R_5$ is hydrogen or lower alkyl and $R_6$ is hydrogen or methyl or $R_5$ and $R_6$ together form an alkylene chain with 3 to 5 carbon atoms, $R_7$ is hydrogen or lower alkyl, Z is an alkylene chain with 2 to 5 carbon atoms or the 2-hydroxypropylene chain, and $X^1$ is a group which can be split off aminolytically selected from the group consisting of halogen, lower alkyl sulphonyl, phenyl sulphonyl, and lower alkyl or halo substituted phenyl sulphonyl.

* * * * *

UNITED STATES PATENT AND TRADEMARK OFFICE
CERTIFICATE OF CORRECTION

PATENT NO. : 4,695,566

DATED : September 22, 1987

INVENTOR(S) : Henning HEINEMANN; Wolfgang KEHRBACH; Uwe SCHOEN; Gerd BUSCHMANN and Ulrich KUHL It is certified that error appears in the above—identified patent and that said Letters Patent is hereby corrected as shown below:

Column 23, line 20 (Claim 1), "hydrogen, hydrogen," should read -- hydrogen, halogen, --;

line 68 (Claim 5), "and" should read -- or --.

Column 24, line 47 (Claim 13), "3-[1-2-pyrrolidinoethylaminocarbonyl)-propyl-1-" should read -- 3-[1-(2-pyrrolidinoethylaminocarbonyl)-propyl-1- --;

line 51 (Claim 14), "antianythmic" should read -- antiarrythmic --;

line 52 (Claim 14), "antianythmic" should read -- antiarrythmic --.

Signed and Sealed this

Twelfth Day of July, 1988

Attest:

DONALD J. QUIGG

Attesting Officer

Commissioner of Patents and Trademarks